(12) United States Patent
Zhang et al.

(10) Patent No.: US 9,029,571 B2
(45) Date of Patent: May 12, 2015

(54) DEVICE AND METHOD FOR EVALUATING ORGANIC MATERIAL FOR ORGANIC SOLAR CELL

(75) Inventors: Zhenfeng Zhang, Tokyo (JP); Tsuneo Imamoto, Chiba (JP); Ken Tamura, Tokyo (JP)

(73) Assignee: Nippon Chemical Industrial Co., Ltd., Tokyo (JP)

( * ) Notice: Subject to any disclaimer, the term of this patent is extended or adjusted under 35 U.S.C. 154(b) by 0 days.

(21) Appl. No.: 14/126,683

(22) PCT Filed: Jun. 21, 2012

(86) PCT No.: PCT/JP2012/065831
§ 371 (c)(1),
(2), (4) Date: Mar. 7, 2014

(87) PCT Pub. No.: WO2012/176830
PCT Pub. Date: Dec. 27, 2012

(65) Prior Publication Data
US 2014/0213800 A1      Jul. 31, 2014

(30) Foreign Application Priority Data
Jun. 23, 2011 (JP) .................................. 2011-139947

(51) Int. Cl.
| C07F 9/28 | (2006.01) |
| C07F 9/655 | (2006.01) |
| C07B 53/00 | (2006.01) |
| C07F 15/00 | (2006.01) |
| C07C 231/18 | (2006.01) |

(52) U.S. Cl.
CPC ............... *C07F 9/28* (2013.01); *C07F 9/65517* (2013.01); *C07B 53/00* (2013.01); *C07F 15/0073* (2013.01); *C07C 231/18* (2013.01)

(58) Field of Classification Search
USPC ........................................................ 549/220
See application file for complete search history.

(56) References Cited

U.S. PATENT DOCUMENTS

| 2007/0021610 A1 | 1/2007 | Imamoto et al. |
| 2011/0098485 A1 | 4/2011 | Pugin et al. |
| 2011/0118482 A1 | 5/2011 | Pugin et al. |

FOREIGN PATENT DOCUMENTS

| JP | 2000-319288 A | 11/2000 |
| JP | 2007-056007 A | 3/2007 |
| JP | 2011-503220 A | 1/2011 |
| JP | 2011-503221 A | 1/2011 |
| WO | 2011/126045 A1 | 10/2011 |
| WO | 2012/005200 A1 | 1/2012 |

OTHER PUBLICATIONS

Imamoto, Tsuneo et al., "Improved synthetic routes to methylene-bridged P-chiral diphosphine ligands via secondary phosphine-boranes", Tetrahedron: Asymmetry, 2010, vol. 21, pp. 1522-1528.
Imamoto, Tsuneo et al., "Rigid P-Chiral Phosphine Ligands with tert-Butylmethylphosphino Groups for Rhodium-Catalyzed Asymmetric Hydrogenation of Functionalized Alkenes", Journal of the American Chemical Society, 2012, vol. 134, pp. 1754-1769.
International Search Report of PCT/JP2012/065831, mailing date of Sep. 4, 2012.

*Primary Examiner* — Kristin Vajda
(74) *Attorney, Agent, or Firm* — Westerman, Hattori, Daniels & Adrian, LLP

(57) ABSTRACT

Provided are a novel 1,2-bis(dialkylphosphino)-4,5-(methylenedioxy)benzene derivative that forms a metal complex having particularly high asymmetry induction capacity and catalytic activity on β-dehydroamino acids, a method for manufacturing the same, a metal complex having this 1,2-bis(dialkylphosphino)-4,5-(methylenedioxy)benzene derivative as a ligand, and an asymmetric hydrogenation method using this metal complex. A 1,2-bis(dialkylphosphino)-4,5-(methylenedioxy)benzene derivative represented by general formula (1). (In the formula, $R^1$ and $R^2$ represent an alkyl group having 1-10 carbon atoms, and $R^1$ and $R^2$ have different numbers of carbon atoms.)

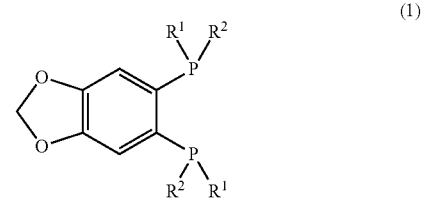

(1)

13 Claims, No Drawings

The present invention relates to a novel 1,2-bis(dialkylphosphino)-4,5-(methylenedioxy)benzene derivative and a method for producing the same. The 1,2-bis(dialkylphosphino)-4,5-(methylenedioxy)benzene derivative can be used as a ligand for asymmetric synthesis catalysts. The present invention also relates to a metal complex having the 1,2-bis(dialkylphosphino)-4,5-(methylenedioxy)benzene derivative as a ligand and an asymmetric hydrogenation method using the metal complex.

BACKGROUND ART

An optically active phosphine ligand having an asymmetric center on a phosphorous atom plays an important role in a catalytically asymmetric synthesis reaction using a transition metal complex. A 1,2-bis(dialkylphosphino)benzene derivative has been suggested as an optically active phosphine ligand having an asymmetric center on a phosphorous atom in Patent Literature 1.

In Patent Literature 2, a 2,3-bis(dialkylphosphino)pyrazine derivative has been suggested. This pyrazine derivative is characterized in that its electron-withdrawing property, which is derived from a pyrazine skeleton, is very high and that because of this the electron density of the phosphorous atom in the phosphine moiety is low. It is effective to use a metal complex having this pyrazine derivative as a ligand as a catalyst for a reaction in which this feature is exploited.

Although an asymmetric hydrogenation reaction from β-dehydroamino acid to β-amino acid using a rhodium catalyst is widely known in general, catalysts that have high asymmetric induction ability and catalytic activity on both E and Z forms of β-dehydroamino acids, other than catalysts using 1,2-bis(dialkylphosphino)benzene derivatives and 2,3-bis(dialkylphosphino)pyrazine derivatives, are not known well.

CITATION LIST

Patent Literature

Patent Literature 1

Japanese Patent Laid-Open No. 2000-319288

Patent Literature 2

Japanese Patent Laid-Open No. 2007-56007

SUMMARY OF INVENTION

Technical Problem

In advancing the study of an optically active phosphine ligand having an asymmetric center on a phosphorous atom, the present inventors have found a novel 1,2-bis(dialkylphosphino)-4,5-(methylenedioxy)benzene derivative that has high asymmetric induction ability and catalytic activity especially on β-dehydroamino acid, and thus have completed the present invention.

Therefore, the object of the present invention is to provide a novel 1,2-bis(dialkylphosphino)-4,5-(methylenedioxy) benzene derivative that forms a metal complex having high asymmetric induction ability and catalytic activity especially on β-dehydroamino acid, a method for producing the same, a metal complex having the 1,2-bis(dialkylphosphino)-4,5-(methylenedioxy)benzene derivative as a ligand, and an asymmetric hydrogenation method using the metal complex.

Solution to Problem

The first invention that the present invention seeks to provide is to provide a 1,2-bis(dialkylphosphino)-4,5-(methylenedioxy)benzene derivative represented by the following general formula (1):

[Formula 1]

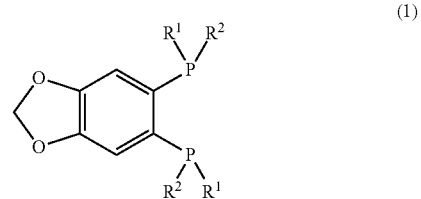

(wherein, $R^1$ and $R^2$ represent an alkyl group having 1 to 10 carbon atoms, and the number of carbon atoms of $R^1$ is different from that of $R^2$).

A second invention that the present invention seeks to provide is a method for producing the 1,2-bis(dialkylphosphino)-4,5-(methylenedioxy)benzene derivative according to the first invention, comprising steps of: deboranating a phosphine-borane compound represented by the following general formula (2), subsequently reacting the deboranated compound with an alkyl magnesium halide compound, then, reacting the product with an alkyldihalogenophosphine represented by the general formula: $R^aPX'_2$ (Ra is one of $R^1$ and $R^2$ in the general formula (1), and X' represents a halogen atom), and subsequently, reacting the product with a Grignard reagent represented by the general formula: $R^bMgX''$ ($R^b$ is one of $R^1$ and $R^2$ in the general formula (1), and X'' represents a halogen atom)

[Formula 2]

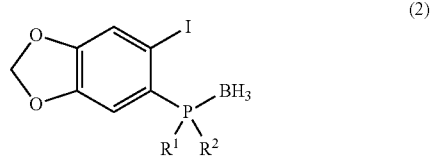

(wherein, $R^1$ and $R^2$ represent an alkyl group having 1 to 10 carbon atoms, and the number of carbon atoms of $R^1$ is different from that of $R^2$).

A third invention that the present invention seeks to provide is a metal complex having the 1,2-bis(dialkylphosphino)-4,5-(methylenedioxy)benzene derivative according to the first invention as a ligand.

A fourth invention that the present invention seeks to provide is an asymmetric hydrogenation method using the metal complex having the 1,2-bis(dialkylphosphino)-4,5-(methylenedioxy)benzene derivative as a ligand according to the third invention.

Advantageous Effects of Invention

According to the present invention, it is possible to provide a novel 1,2-bis(dialkylphosphino)-4,5-(methylenedioxy)

benzene derivative that may form a useful metal complex as a catalyst for asymmetric synthesis reaction. Additionally, according to the production method of the present invention, this 1,2-bis(dialkylphosphino)-4,5-(methylenedioxy)benzene derivative can be easily produced. Furthermore, this metal complex having the 1,2-bis(dialkylphosphino)-4,5-(methylenedioxy)benzene derivative as a ligand has high enantioselectivity and reaction activity when used as a catalyst for an asymmetric synthesis reaction, and particularly, the metal complex having the novel 1,2-bis(dialkylphosphino)-4,5-(methylenedioxy)benzene derivative of the present invention has high asymmetric induction ability and catalytic activity on β-dehydroamino acid.

DESCRIPTION OF EMBODIMENTS

In the 1,2-bis(dialkylphosphino)-4,5-(methylenedioxy) benzene derivative represented by the general formula (1), $R^1$ and $R^2$ in the formula represent an alkyl group having 1 to 10 carbon atoms, and the number of carbon atoms of $R^1$ is different from that of $R^2$. Two $R^1$ in the general formula (1) may be identical to or different from each other. Similarly, two $R^2$ may be identical to or different from each other. The alkyl groups of $R^1$ and $R^2$ include acyclic alkyl groups and alicyclic alkyl groups.

The acyclic alkyl groups include straight-chain alkyl groups and branched alkyl groups. Examples of the straight-chain alkyl groups include those having 1 to 10 carbon atoms, such as a methyl group, an ethyl group, a n-propyl group, a n-butyl group, a n-pentyl group, a n-hexyl group, and a n-heptyl group. Examples of the branched alkyl groups include those having 3 to 10 carbon atoms, such as an isopropyl group, an isobutyl group, a sec-butyl group, a tert-butyl group, an isoheptyl group, an isohexyl group, and a 1,1,3,3-tetramethylbutyl group.

The alicyclic alkyl groups include monocyclic alkyl groups and multicyclic alkyl groups. Examples of the monocyclic alkyl groups include those having 3 to 10 carbon atoms, such as a cyclopropyl group, a cyclobutyl group, a cyclopentyl group, and a cyclohexyl group. Examples of the multicyclic alkyl groups include those having 4 to 10 carbon atoms, such as an adamantyl group.

The 1,2-bis(dialkylphosphino)-4,5-(methylenedioxy)benzene derivative of the present invention represented by the general formula (1) also includes those that have an asymmetric center on a phosphorous atom and show optical activity, represented by the following general formula (1A), as well as those that do not apparently show optical activity because the derivatives are racemic although $R^1$ and $R^2$ are different. Among these, those represented by the following general formula (1A) exert excellent performance as a ligand of metal complexes for asymmetric synthesis catalysts.

[Formula 3]

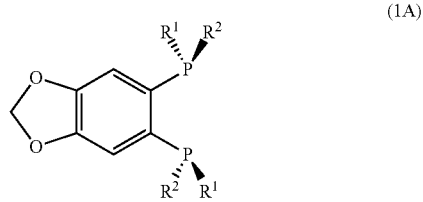

(1A)

(wherein, $R^1$ and $R^2$ represent an alkyl group having 1 to 10 carbon atoms, and the number of carbon atoms of $R^1$ is different from that of $R^2$).

In the general formula (1A), if the number of carbon atoms of $R^1$ is greater, the optically active 1,2-bis(dialkylphosphino)-4,5-(methylenedioxy)benzene derivative represented by the general formula (1A) is the (R,R) form, and if the number of carbon atoms of $R^2$ is greater, the derivative is the (S,S) form.

In the general formula (1A), it is necessary that the number of carbon atoms of each of $R^1$ and $R^2$ is at least one. In the general formula (1A), it is preferred that the group having the greater number of carbon atoms of $R^1$ and $R^2$ is a bulky substituent having steric hindrance. From this viewpoint, as the group having the greater number of carbon atoms of $R^1$ and $R^2$, a secondary alkyl group is more preferred than a primary alkyl group, and a tertiary alkyl group is more preferred than a secondary alkyl group. Alternatively, it is preferred to be an alicyclic alkyl group. Examples of preferable alkyl groups include a tert-butyl group.

At this point, considering that a highly asymmetric space is formed when the 1,2-bis(dialkylphosphino)-4,5-(methylenedioxy)benzene derivative represented by the general formula (1A) is used as a ligand of a metal complex for an asymmetric synthesis catalyst, it is preferred that there is a large difference between the steric hindrance of $R^1$ and that of $R^2$. That is, it is preferred that one of $R^1$ and $R^2$ is a bulky substituent having steric hindrance, namely, a maximal group, whereas the other is a minimal group. Thus, the larger the difference between the number of carbon atoms of $R^1$ and that of $R^2$, the more preferable. Specifically, it is preferred that the difference between the number of carbon atoms of $R^1$ and that of $R^2$ is 2 or more, particularly 3 or more, and more particularly 4 or more. Considering that the group having the smaller number of carbon atoms of $R^1$ and $R^2$ is a minimal group, the acyclic alkyl group is preferred of an alicyclic alkyl group and an acyclic alkyl group having the same number of carbon atoms. Also, among acyclic alkyl groups having the same number of carbon atoms, a straight-chain alkyl group is preferable than a branched alkyl group. Finally, it can be said that the most preferred group as the group having the smaller number of carbon atoms of $R^1$ and $R^2$ is a methyl group. However, generally, a group to be used as the group having the smaller number of carbon atoms is relatively determined based on the relationship with the group having the greater number of carbon atoms. Examples of the preferred combination of $R^1$ and $R^2$ include a combination of $R^1$=a tert-butyl group and $R^2$=a methyl group; and a combination of $R^1$=a methyl group and $R^2$=a tert-butyl group.

Particularly preferred examples of the 1,2-bis(dialkylphosphino)-4,5-(methylenedioxy)benzene derivative represented by the general formula (1) include the following compounds: (R,R)-1,2-bis(tert-butylmethylphosphino)-4,5-(methylenedioxy)benzene, (S,S)-1,2-bis(tert-butylmethylphosphino)-4,5-(methylenedioxy)benzene, (R,R)-1,2-bis(adamantylmethylphosphino)-4,5-(methylenedioxy)benzene, (S,S)-1,2-bis(adamantylmethylphosphino)-4,5-(methylenedioxy)benzene, (R,R)-1,2-bis(isopropylmethylphosphino)-4,5-(methylenedioxy)benzene, (S,S)-1,2-bis(isopropylmethylphosphino)-4,5-(methylenedioxy)benzene, (R,R)-1,2-bis(1,1,3,3-tetramethylbutylmethylphosphino)-4,5-(methylenedioxy)benzene, (S,S)-1,2-bis(1,1,3,3-tetramethylbutylmethylphosphino)-4,5-(methylenedioxy)benzene.

A preferable method for producing the 1,2-bis(dialkylphosphino)-4,5-(methylenedioxy)benzene derivative represented by the general formula (1) is described below.

In the production method of the present invention, first of all, a phosphine-borane compound represented by the following general formula (2) is provided. In this production method, by use of the phosphine-borane compound represented by the following general formula (2) as a starting material, it is possible to obtain the corresponding 1,2-bis(dialkylphosphino)-4,5-(methylenedioxy)benzene derivative represented by the general formula (1). Alternatively, in order to produce its optical active form, a 1,2-bis(dialkylphosphino)-4,5-(methylenedioxy)benzene derivative represented by the general formula (1A), a phosphine-borane compound represented by the following general formula (2A), which is an optically active form of the phosphine-borane compound represented by the general formula (2), may be used as a starting material, instead of the phosphine-borane compound represented by the general formula (2), to perform reactions in the first to the fourth steps described below.

[Formula 4]

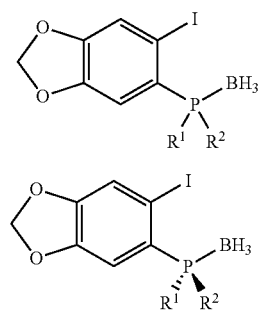

(wherein, $R^1$ and $R^2$ are the same as in the general formula (1)).

The compound of the general formula (2), which is the starting material, can be synthesized, for example, according to the following reaction equation (1).

[Formula 5]

Reaction equation (1)

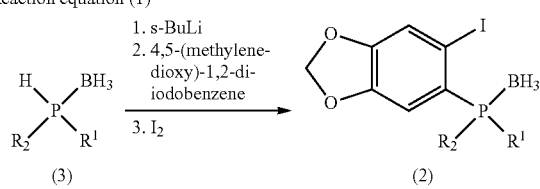

(wherein, $R^1$ and $R^2$ are the same as described above).

In the reaction equation (1), s-BuLi is first added to the starting material, dialkylphosphine-borane (3), at −80° C. under an argon atmosphere to produce phosphide anions. Then, it is possible to obtain the intended phosphine-borane compound represented by the general formula (2) by reacting the phosphide anions with 4,5-(methylenedioxy)-1,2-diiodobenzene (Organic Letters, 2010, Vol. 12, No. 19, 4400-4403). Alternatively, in order to obtain the optically active phosphine-borane compound represented by the general formula (2A), a reaction may be performed by using an optically active form of dialkylphosphine-borane (3) in the reaction according to the reaction equation (1).

Dialkylphosphine-borane (3) and an optically active form thereof can be prepared according to known methods such as the methods described in Japanese Patent Laid-Open No. 2001-253889 and Japanese Patent Laid-Open No. 2007-70310.

In the phosphine-borane compound represented by the general formula (2A), in the case where the number of carbon atoms of $R^1$ is made greater than the number of carbon atoms of $R^2$ (in the case where the phosphine-borane is the R form), the S form is used as dialkylphosphine-borane. In contrast to this, in the phosphine-borane compound represented by the general formula (2A), in the case where the number of carbon atoms of $R^2$ is made greater than the number of carbon atoms of $R^1$ (in the case where the phosphine-borane compound is the S form), the R form is used as dialkylphosphine-borane.

Deboranation of the dialkylphosphine-borane compound of the general formula (2), which is the first step in the production method of the present invention, is represented by the following reaction equation (2).

Reaction equation (2)

[Formula 6]

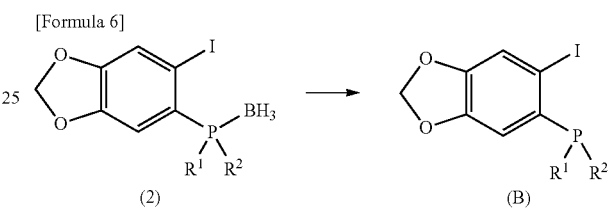

(wherein, $R^1$ and $R^2$ are the same as described above).

The deboranation of the alkylphosphine-borane compound according to the reaction equation (2) can be performed in accordance with the conventional known methods. The deboranation can be performed in an organic solvent such as THF, hexane, toluene, and dimethoxyethane in the presence of a base such as 1,4-diazabicyclo[2.2.2]octane (DABCO), N-methylmorpholine, triethylamine, pyrrolidine, and diethylamine. It is preferred that, among these, DABCO is used as a base. It is preferred that the amount of the base to be used is 1 to 3 moles per mole of the phosphine-borane compound represented by the general formula (2). Additionally, the reaction time can be set to 0.5 hour to 5 hours. The reaction temperature can be set to 20 to 110° C.

Next, metal-halogen exchange reaction with an alkyl magnesium halide compound is performed as the second step. The alkyl magnesium halide compound is represented by the general formula RMgX (wherein, R represents a straight-chain or branched alkyl group having 1 to 5 carbon atoms, and X represents a halogen atom). The reaction with the alkyl magnesium halide compound is represented by the following reaction equation (3).

[Formula 7]

Reaction equation (3)

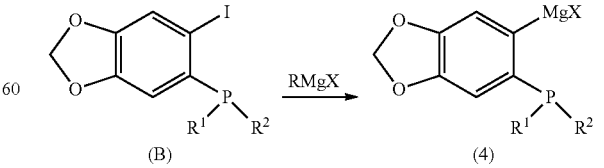

(wherein, $R^1$, $R^2$, R and X are the same as described above).

The reaction with the alkyl magnesium halide compound is performed in an organic solvent such as THF, hexane, toluene, and dimethoxyethane. Examples of the alkyl magnesium halide compound include methyl magnesium chloride, methyl magnesium bromide, ethyl magnesium chloride, ethyl magnesium bromide, n-propyl magnesium chloride, n-propyl magnesium bromide, isopropyl magnesium chloride, isopropyl magnesium bromide, n-butyl magnesium chloride, sec-butyl magnesium chloride, and tert-butyl magnesium chloride. Among these, isopropyl magnesium chloride is preferred. The amount of the alkyl magnesium halide compound to be used is preferably 0.7 to 2.0 moles and particularly preferably 1.0 to 1.5 moles per mole of the phosphine-borane compound represented by the general formula (2) used in the first step. Alternatively, in this second step, it is possible to allow the reaction to proceed more efficiently, by performing the reaction under coexistence of a reaction aid such as lithium chloride, lithium bromide, lithium iodide, lithium tetrafluoroborate, and lithium perchlorate, as required. The amount of this reaction aid to be added is in a molar ratio of 0.2 to 4.0, preferably 1.0 to 1.5 relative to the alkyl magnesium halide compound.

Additionally, the reaction time can be set to 10 minutes to 8 hours and preferably to 20 minutes to 2 hours. The reaction temperature can be set to −80 to 80° C.

Then, as the third step, the reaction product (4) of the second step is reacted with alkyldihalogenophosphine represented by the general formula $R^aPX'_2$ ($R^a$ is one of $R^1$ and $R^2$ in the general formula (1), and X' represents a halogen atom). It is preferred that $R^a$ is the group having the greater number of carbon atoms of $R^1$ and $R^2$. Examples of the halogen atom represented by X' include fluorine, chlorine, bromine, and iodine, and chlorine is preferred. The alkyldihalogenophosphine represented by the general formula $R^aPX'_2$ is commercially available. Additionally, it is possible to industrially produce the alkyldihalogenophosphine inexpensively (for example, see Japanese Patent Laid-Open No. 2002-255983 and Japanese Patent Laid-Open No. 2001-354683). For example, in the case where $R^a$ is $R^1$, the reaction of the third step is represented by the following reaction equation (4).

Reaction equation (4) [Formula 8]

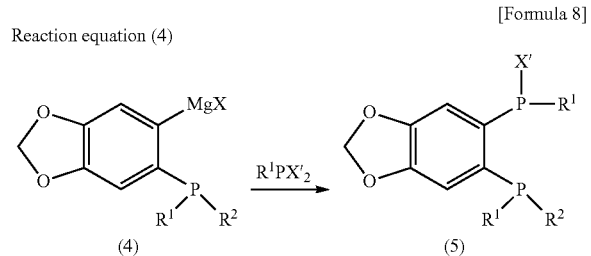

(wherein, $R^1$, $R^2$, X and X' are the same as described above).

The reaction of the third step can be performed in an organic solvent such as THF, hexane, toluene, and dimethoxyethane. The amount of the alkyldihalogenophosphine represented by the general formula $R^aPX'_2$ to be used is preferably 1.0 to 2.0 moles per mole of the phosphine-borane compound represented by the general formula (2) used in the first step. Additionally, the reaction time can be set to 0.5 hour to 24 hours. The reaction temperature can be set to −100 to 80° C.

Then, as the fourth step, the reaction product (5) of the third step is reacted with a Grignard reagent represented by the general formula $R^bMgX''$ ($R^b$ is one of $R^1$ and $R^2$ in the general formula (1), and X'' represents a halogen atom). In this case, $R^b$ is a group that is different from $R^a$ between $R^1$ and $R^2$ in the general formula (1).

Examples of the halogen atom represented by X'' include fluorine, chlorine, bromine, and iodine, and chlorine and bromine are preferred. For example, in the case where $R^b$ is $R^2$, the reaction of the fourth step is represented by the following reaction equation (5).

Reaction equation (5) [Formula 9]

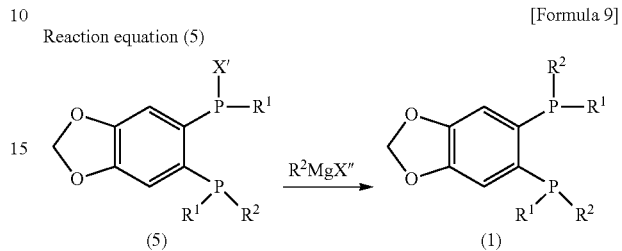

(wherein, $R^1$, $R^2$, and X'' are the same as described above).

The reaction of the fourth step can be performed in accordance with the conventional known Grignard reaction. The reaction can be performed in an organic solvent such as THF, hexane, toluene, and dimethoxyethane. The amount of the Grignard reagent represented by the general formula $R^bMgX''$ to be used is preferably 1.0 to 2.0 moles per mole of the phosphine-borane compound represented by the general formula (2) used in the first step. Additionally, the reaction time can be set to 0.5 hour to 24 hours. The reaction temperature can be set to 0 to 100° C. Note that it is preferred that the reactions of the above-described the first to the fourth steps are performed under inert gas.

In accordance with the first to the fourth steps described above, 1,2-bis(dialkylphosphino)-4,5-(methylenedioxy)benzene derivative represented by the general formula (1) or the optically active 1,2-bis(dialkylphosphino)-4,5-(methylenedioxy)benzene derivative represented by the general formula (1A), which is the objective material, can be obtained, and it is possible to obtain the object material in a higher purity by performing purification in accordance with the routine procedure, as required.

Alternatively, in the case where the optically active 1,2-bis(dialkylphosphino)-4,5-(methylenedioxy)benzene derivative represented by the general formula (1A) is obtained, the 1,2-bis(dialkylphosphino)-4,5-(methylenedioxy)benzene derivative, which is an objective material, is the (R,R) form or the (S,S) form, but a mixture that includes the (R,S) form or the (S,R) form, for example the meso form other than the objective material may be obtained after the first to the fourth steps. For example, in the case where the objective material is the (R,R) form, and two $R^1$ are the same alkyl groups and two $R^2$ are the same alkyl groups, a mixture of the (R,R) form and the meso form may be obtained. Thus, if the (R,R) form or the (S,S) form, which is the objective material of the present invention, is separated from the mixture by performing purification (a) as required, the objective material can be obtained in a higher purity. This separation may be performed in accordance with an ordinary purification method, and generally, recrystallization is sufficient. The separation can also be performed in column separation, as required. Additionally, in performing purification (a), it is preferred that further purification (a') is performed using purification methods such as desolvation, washing, and column separation, as appropriate.

Alternatively, in the case where the objective material is prone to be oxidized and difficult to purify in purification steps such as column separation, in order to suppress oxidization during purification operation for the 1,2-bis(dialkylphos-phino)-4,5-(methylenedioxy)benzene derivative as required, it is preferred that, by performing the fifth step as described below subsequent to the first to the fourth steps, the 1,2-bis(dialkylphosphino)-4,5-(methylenedioxy)benzene derivative is boranated to derive the corresponding 1,2-bis(dialkylphosphino)-4,5-(methylenedioxy)benzene-borane derivative represented by the following general formula (1-1) or (1-1A), which is subsequently purified.

[Formula 10]

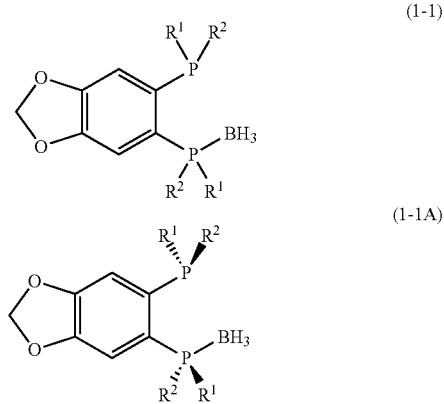

(wherein, $R^1$ and $R^2$ are the same as described above).

The reaction of the fifth step can be performed in accordance with the conventional known boranation reaction. As boranating agents to be used for boranation, a borane-THF complexes, alkali metal borohydrides, and borane-amine complexes can be used.

The alkali metal borohydride is represented by the chemical formula $MBH_4$ (wherein, M represents an alkali metal atom), and is preferably lithium borohydride ($LiBH_4$), sodium borohydride ($NaBH_4$) and potassium borohydride ($KBH_4$).

The borane-amine complex is a complex represented by the chemical formula $BH_3 \cdot R^3{}_n H_{(3-n)} N$ (wherein, $R^3$ represents alkyl, cycloalkyl, aryl, and cycloaryl groups, which may be the same or different groups, and when n is 2 or more, two $R^3$ may form a ring, and n is an integer of 0 to 3), that is, a complex of borane ($BH_3$) with ammonia, primary amine, secondary amine, or tertiary amine. Examples of the borane-amine complex specifically include a borane-ammonia complex, a borane-tert-butylamine complex, a borane-dimethylamine complex, a borane-triethylamine complex, a borane-trimethylamine complex, a borane-4-ethylmorpholine complex, a borane-2,6-lutidine complex, a borane-morpholine complex, a borane-4-methylmorpholine complex, a borane-4-phenylmorpholine complex, a borane-piperazine complex, a borane-pyridine complex, a borane-N,N-diethylaniline complex, and a borane-N,N-diisopropylaniline complex.

The reaction according to the fifth step can be performed in an organic solvent such as THF, hexane, toluene, and dimethoxyethane.

The amount of the boranating agent to be used is preferably 1.0 to 3.0 moles per mole of the phosphine-borane compound represented by the general formula (2) or the general formula (2A) used in the first step. Additionally, the reaction time can be set to 0.5 to 5.0 hours. The reaction temperature can be set to −50 to 50° C. Note that it is preferred that the reaction of the fifth step is performed under inert gas.

After the fifth step is finished, desired purification is performed, and then, the purified 1,2-bis(dialkylphosphino)-4,5-(methylenedioxy)benzene-borane derivative is deboranated to obtain the 1,2-bis(dialkylphosphino)-4,5-(methylenedioxy)benzene derivative represented by the general formula (1) or the general formula (1A) again.

This deboranation can be performed in accordance with the conventional known methods. The deboranation can be performed in an organic solvent such as THF, hexane, toluene, and dimethoxyethane in the presence of a base such as 1,4-diazabicyclo[2.2.2]octane (DABCO), N-methylmorpholine, triethylamine, pyrrolidine, and diethylamine. It is preferred that, among these, DABCO is used as a base. The amount of the base to be used is preferably 1 to 3 moles per mole of the 1,2-bis(dialkylphosphino)-4,5-(methylenedioxy)benzene-borane derivative represented by the general formula (1-1) or the general formula (1-1A). Additionally, the reaction time can be set to 0.5 to 5 hours. The reaction temperature can be set to 20 to 110° C.

The phosphine-borane compound represented by the general formula (2), which is used in the production method of the present invention as a starting material, has one —$PR^1R^2BH_3$ group, and the compound represented by the general formula (B), which is obtained by the deboranation of the compound, has one —$PR^1R^2$ group. In the present production method, by performing metal-halogen exchange reaction using the alkyl magnesium halide compound (RMgX), the site in which an iodine group is attached on the benzene ring becomes a carbon anion. Subsequently, by adding an alkyldihalogenophosphine, it is possible to introduce a —$PR^1R^2$ group onto the site to which an iodine group has been originally attached.

Alternatively, it may be difficult to directly introduce another —$PR^1R^2$ group onto the MgX site of the compound because of the steric hindrance due to the bulkiness of the —$PR^1R^2$ group. Thus, in the present invention, an alkyl group $R^1$ having a greater number of carbon atoms is first introduced onto the compound represented by the general formula (B) having one —$PR^1R^2$ group together with a phosphorous atom, and then, another alkyl group $R^2$ having a smaller number of carbon atoms is introduced thereon. Through performing this stepwise step, it is possible to easily introduce a —$PR^1R^2$ group even if the group is bulky.

Additionally, according to the production method of the present invention, since the first to the fourth steps and further, the first to the fifth steps can be performed sequentially, the method has an advantage that the objective 1,2-bis(dialkylphosphino)-4,5-(methylenedioxy)benzene derivative can be industrially advantageously obtained.

The 1,2-bis(dialkylphosphino)-4,5-(methylenedioxy)benzene derivative represented by the general formula (1) and the general formula (1A) obtained by the production method of the present invention can form a complex with a transition metal, as a ligand. Particularly, a metal complex having the optically active 1,2-bis(dialkylphosphino)-4,5-(methylenedioxy)benzene derivative represented by the general formula (1A) as a ligand is useful as a an asymmetric synthesis catalyst.

Examples of a transition metal capable of forming a complex include rhodium, ruthenium, iridium, palladium, nickel, iron, and copper, and rhodium metal is preferred. As a method for forming a complex using the 1,2-bis(dialkylphosphino)-4,5-(methylenedioxy)benzene derivative represented by the general formula (1) and the general formula (1A) as a ligand with rhodium metal, the method described, for example, in Experimental Chemistry, 4th edition (edited by the Chemical Society of Japan, published by Maruzen Co., Ltd., Vol. 18, pp. 327-353) may be followed. For example, it is possible to produce a rhodium complex by reacting 1,2-bis(dialkylphosphino)-4,5-(methylenedioxy)benzene derivative represented by the general formula (1) with bis(cyclooctane-1,5-diene) rhodium hexafluoroantimonate, bis(cyclooctane-1,5-diene) rhodium tetrafluoroborate or the like.

Specific examples of the rhodium complex to be obtained include [Rh((S,S)-(A))(cod)]Cl, [Rh((S,S)-(A))(cod)]Br, [Rh((S,S)-(A))(cod)]I, [Rh((R,R)-(A))(cod)]Cl, [Rh((R,R)-(A))(cod)]Br, [Rh((R,R)-(A))(cod)]I, [Rh((S,S)-(A))(cod)]SbF$_6$, [Rh((S,S)-(A))(cod)]BF$_4$, [Rh((S,S)-(A))(cod)]ClO$_4$, [Rh((S,S)-(A))(cod)]PF$_6$, [Rh((S,S)-(A))(cod)]BPh$_4$, [Rh((R,R)-(A))(cod)]SbF$_6$, [Rh((R,R)-(A))(cod)]BF$_4$, [Rh((R,R)-(A))(cod)]ClO$_4$, [Rh((R,R)-(A))(cod)]PF$_6$, [Rh((R,R)-(A))(cod)]BPh$_4$, [Rh((R,R)-(A))(cod)]SbF$_6$, [Rh((S,S)-(A))(nbd)]PF$_6$, [Rh((S,S)-(A)) (nbd)]SbF$_6$, [Rh((S,S)-(A))(nbd)]BF$_4$, [Rh((S,S)-(A)) (nbd)]ClO$_4$, [Rh((S,S)-(A))(nbd)]BPh$_4$, [Rh((R,R)-(A))(nbd)]PF$_6$, [Rh((R,R)-(A))(nbd)]SbF$_6$, [Rh((R,R)-(A))(nbd)]BF$_4$, [Rh((R,R)-(A))(nbd)]ClO$_4$, [Rh((R,R)-(A))(nbd)]BPh$_4$ or the like, and in the present invention [Rh((S,S)-(A))(cod)]SbF$_6$, [Rh((R,R)-(A))(cod)]SbF$_6$, [Rh((S,S)-(A))(nbd)]SbF$_6$, [Rh((R,R)-(A))(nbd)]SbF$_6$ are preferred. Meanwhile, (A) in the above-described rhodium complexes represents the 1,2-bis(dialkylphosphino)-4,5-(methylenedioxy)benzene derivative represented by the general formula (1) or the general formula (1A), cod represents 1,5-cyclooctadiene, nbd represents norbornadiene, and Ph represents phenyl.

A transition metal complex having the optically active 1,2-bis(dialkylphosphino)-4,5-(methylenedioxy)benzene derivative represented by the general formula (1A) as a ligand (hereinafter, also referred to as a transition metal complex according to the present invention) is useful as an asymmetric synthesis catalyst. Examples of such asymmetric synthesis reaction include asymmetric hydrogenation reaction, asymmetric hydrosilylation reaction, and asymmetric Michael addition reaction. These asymmetric synthesis reactions can be performed in the same manner as usual, except that the transition metal complex according to the present invention is used.

The transition metal complex according to the present invention is particularly suitable as a catalyst for an asymmetric hydrogenation reaction. Examples of the compound used as a substrate in an asymmetric hydrogenation reaction include compounds having a C=C double bond, C=O double bond, or a C=N double bond containing a prochiral carbon atom. Examples of the compound include α-dehydroamino acids, β-dehydroamino acids, itaconic acid, enamides, β-ketoesters, enol esters, α,β unsaturated carboxylic acids, β,γ unsaturated carboxylic acids, and imines. Particularly, the transition metal complex according to the present invention is characteristic of having high asymmetric induction ability and catalytic activity on β-dehydroamino acid. Additionally, in an asymmetric hydrogenation reaction, it is preferred that the molar ratio between the substrate and the transition metal complex according to the present invention, which is a catalyst, (substrate/catalyst) is usually 100 or more.

Alternatively, the metal complex that has the 1,2-bis(dialkylphosphino)-4,5-(methylenedioxy)benzene derivative represented by the general formula (1) or the general formula (1A) of the present invention as a ligand and that is formed with a transition metal selected from a group consisting of gold, silver and copper (preferably gold) is expected to be utilized as an anticancer agent, as well as a 2,3-bis(dialkylphosphino)pyrazine derivative described in Japanese Patent Laid-Open No. 2007-320909. This metal complex is represented by [ML$_2$]$^+$X$^-$, wherein L represents the 1,2-bis(dialkylphosphino)-4,5-(methylenedioxy)benzene derivative of the present invention.

EXAMPLES

Hereinbelow, the invention is described in detail according to Examples, but the present invention is not intended to be limited to these Examples.

Synthesis Example 1

Synthesis of 1,2-diiodo-4,5-(methylenedioxy)benzene

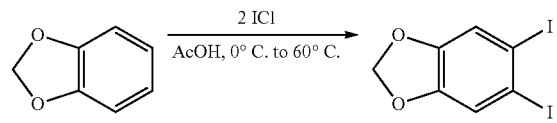

[Formula 11]

To an acetic acid solution (30 mL) of 1,2-(methylenedioxy) benzene (7.50 g, 0.06 mol) cooled to 0° C., an acetic acid solution (15 mL) of iodine chloride (25.00 g, 0.15 mol) was added dropwise for 15 minutes, then the temperature was increased to 60° C., and the reaction was performed for 2 hours. Thereafter, the reaction liquid was poured with vigorously stirring into diethyl ether (100 mL) and ice water (100 mL). To the dark red solution, Na$_2$SO$_3$ was added, and the brown organic layer was separated. Diethyl ether (100 mL×2) was added to the water tank to separate the organic layer, and then, the obtained organic layer was washed with a saline solution (50 mL) and dried over Na$_2$SO$_4$. Light yellow crystals precipitated after concentration of the solvent were filtered and washed with methanol to obtain 1,2-diiodo-4,5-(methylenedioxy)benzene (9.95 g, 0.027 mol) as white crystals in a yield of 46%.

Identification Data of 1,2-diiodo-4,5-(methylenedioxy)benzene $^1$H NMR (500 MHz, CDCl$_3$): δ 7.30 (s, 2H), 5.97 (s, 2H).

Synthesis Example 2

Synthesis of (R)-2-(boranato-tert-butylmethylphosphino)-1-iodo-4,5-(methylenedioxy)benzene

[Formula 12]

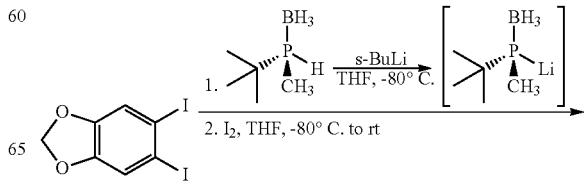

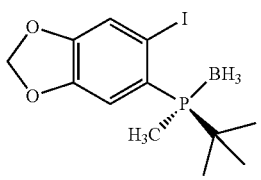

To a THF solution (15 mL) of (S)-tert-butylmethylphosphineborane (0.48 g, 4.0 mmol) cooled to −80° C., s-BuLi (1.07 M cyclohexane/n-hexane) (11.2 mL, 12.0 mmol) was added and stirred for 30 minutes. A THF solution (5 mL) of 1,2-diiodo-4,5-(methylenedioxy)benzene (1.95 g, 5.2 mmol) was slowly added thereto for 10 minutes. Then, a THF solution (1.5 mL) of iodine (1.52 g, 6.0 mmol) was added and the temperature was increased to the room temperature. The solvent was concentrated and extracted with ethyl acetate (30 mL×2). The obtained organic layer was washed with a saline solution (20 mL) and dried over Na$_2$SO$_4$. A yellow oily material obtained by concentration of the solvent was purified with a silica gel column to obtain (R)-2-(boranato-tert-butylmethylphosphino)-1-iodo-4,5-(methylenedioxy)benzene (0.85 g, 2.3 mmol) as white crystals in a yield of 58%.

Identification Data of (R)-2-(boranato-tert-butylmethylphosphino)-1-iodo-4,5-(methylenedioxy)benzene Mp.=123-135° C., [α]$_D^{27}$=−20 (c 0.5, EtOAc). $^1$H NMR (500 MHz, CDCl$_3$): δ 7.54 (d, J=12.3 Hz, 1H), 7.42 (d, J=1.7 Hz, 1H), 6.03 (dd, J=4.3 Hz, 1.2 Hz, 2H), 1.91 (d, J=10.0 Hz, 3H), 1.20 (d, J=14.4 Hz, 9H). $^{31}$PNMR (202 MHz, CDCl$_3$): δ 39.9 (br).

$^{13}$CNMR (126 MHz, CDCl$_3$): δ 150.7, 148.0 (d, J=16.8 Hz), 124.2 (d, J=48.1 Hz), 122.6 (d, J=7.2 Hz), 188.2 (d, J=19.2 Hz), 102.5, 88.7, 31.9 (d, J=31.2 Hz), 26.4 (d, J=2.4 Hz), 9.7 (d, J=37.3 Hz).

Example 1

Synthesis of (R,R)-1-(tert-butylmethylphosphino)-2-(boranato-tert-butylmethylphosphino)-4,5-(methylenedioxy)benzene (Compound 1C)

[Formula 13]

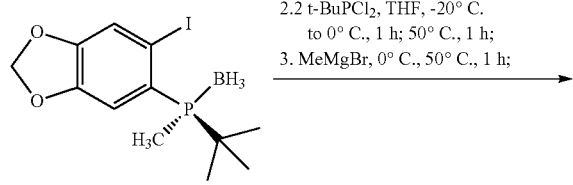

1. DABCO, THF, 65° C., 1 h;
2.1 i-PrMgCl, LiCl, −20° C., 15 min;
2.2 t-BuPCl$_2$, THF, −20° C. to 0° C., 1 h; 50° C., 1 h;
3. MeMgBr, 0° C., 50° C., 1 h;

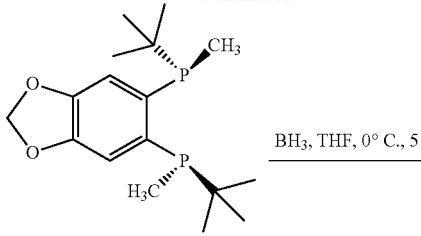

(1B)

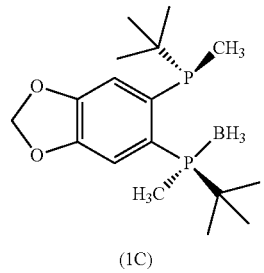

(1C)

Under an argon atmosphere, a THF solution (1.5 mL) of (R)-2-(boranato-tert-butylmethylphosphino)-1-iodo-4,5-(methylenedioxy)benzene (182 mg, 0.50 mmol) and 1,4-diazabicyclo[2.2.2]octane (62 mg, 0.55 mmol) was gently heated and refluxed for one hour. Subsequently, after cooling to −20° C., a THF solution of 1.3 M i-PrMgCl.LiCl (0.42 mL, 0.55 mmol) was added, and, after 10 minutes, a THF solution (1.0 mL) of t-BuPCl$_2$ (119 mg, 0.75 mmol) was slowly added. After the temperature was increased to 0° C., stirring was performed for one hour. The temperature was further increased to 50° C., and stirring was performed for one hour. Then, after cooling to 0° C., a THF solution of 1.12 M MeMgBr (1.34 mL, 1.5 mmol) was added. After the temperature was increased to 50° C., a reaction was performed under stirring for one hour. When the reaction solution was analyzed with LC-MS (APCI), a molecular ion peak of 327 [M+H]$^+$ was detected. Therefore, it was able to confirm that (R,R)-1,2-bis(tert-butylmethylphosphino)-4,5-(methylenedioxy)benzene (Compound 1B) was contained in the reaction liquid.

Then, after cooling to 0° C., a THF solution of 1.06 M BH$_3$.THF complex (1.88 mL, 2.0 mmol) was added. Thereafter, the reaction was quenched by addition of water, and ethyl acetate (15 mL×2) was added to separate the organic layer. The obtained organic layer was washed with a saline solution and dried over Na$_2$SO$_4$. A crude product obtained by concentration of the solvent was purified with a silica gel column to obtain (R,R)-1-(tert-butylmethylphosphino)-2-(boranato-tert-butylmethylphosphino)-4,5-(methylenedioxy)benzene (Compound 1C)(50 mg, 0.15 mmol) as white crystals in a yield of 29%.

Identification Data of Compound 1C

Mp.=131-132° C., [α]$_D^{27}$=−24 (c 0.5, EtOAc). $^1$HNMR (500 MHz, CDCl$_3$): δ 7.37 (dd, J=10.9 Hz, 1.8 Hz, 1H), 7.23 (d, J=2.3 Hz, 1H), 6.25 (dd, J=4.0 Hz, 0.9 Hz, 2H), 1.81 (d, J=9.2 Hz, 3H), 1.19 (d, J=13.8 Hz, 9H), 1.18 (s, 3H), 1.09 (d, J=12.6 Hz, 9H).

$^{31}$PNMR (202 MHz, CDCl$_3$): δ 34.2 (br), −20.0.

$^{13}$CNMR (126 MHz, CDCl$_3$): δ 149.3, 148.2 (d, J=15.6 Hz), 140.4 (dd, J=32.5 Hz, 9.8 Hz), 129.0 (dd, J=46.9 Hz, 39.7 Hz), 115.5 (t, J=13.2 Hz), 113.0 (d, J=10.8 Hz), 101.9, 30.2 (d, J=57.7 Hz), 30.2 (d, J=9.6 Hz), 28.5 (d, J=14.4 Hz), 26.8 (d, J=2.4 Hz), 11.8 (dd, J=37.3 Hz, 21.6 Hz), 9.7 (d, J=22.8 Hz).

Example 2

Synthesis of (R,R)-1,2-bis(tert-butylmethylphosphino)-4,5-(methylenedioxy)benzene (Compound 1B)

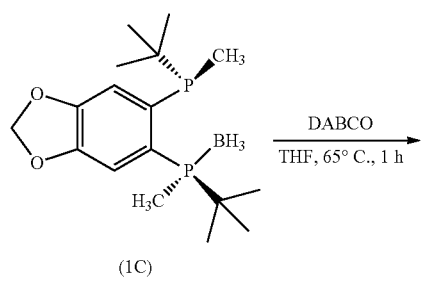

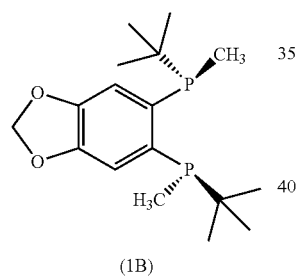

Under an argon atmosphere, a THF solution (5 mL) of (R,R)-1-(tert-butylmethylphosphino)-2-(boranato-tert-butylmethylphosphino)-4,5-(methylenedioxy)benzene (Compound 1C) (0.15 g, 0.44 mmol) and 1,4-diazabicyclo[2.2.2]octane (0.12 g, 0.55 mmol) was gently heated and refluxed for one hour. After the solvent was distilled off, degassed hexane (5 mL) was added using a syringe, and the slurry was filtered to remove the solid. The hexane solution was concentrated to obtain a light yellow viscous material, to which methanol was added to obtain white crystals. Additionally, by recrystallization from methanol, (R,R)-1,2-bis(tert-butylmethylphosphino)-4,5-(methylenedioxy)benzene (Compound 1B) (0.10 mg, 0.31 mmol) was obtained as white crystals in the yield of 70%.

Identification Data of Compound 1B

Mp.=146-148, $[\alpha]_D^{25}$=+63.3.

$^1$H NMR (500 MHz, CDCl$_3$): δ 7.00-6.95 (m, 2H), 5.98 (s, 2H), 1.18 (t, J=3.4 Hz, 6H), 0.96 (t, J=6.0 Hz, 18H).

$^{31}$P NMR (202 MHz, CDCl$_3$): δ −24.9 (s).

$^{13}$C NMR (126 MHz, CDCl$_3$): δ 147.8, 138.7 (t, J=7.2 Hz), 111.1, 101.1, 30.5 (t, J=7.8 Hz), 27.3 (t, J=7.8 Hz), 6.2 (t, J=5.4 Hz)

Example 3

Synthesis of ((R,R)-1,2-bis(tert-butylmethylphosphino)-4,5-(methylenedioxy)benzene)(1,5-cyclooctadiene)rhodium(1+)hexafluoroantimonate (Compound 1D)

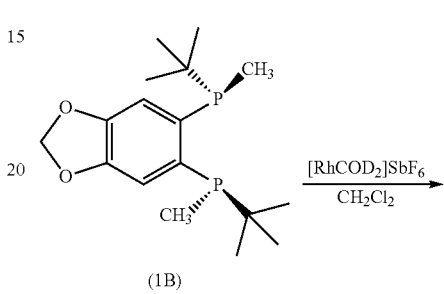

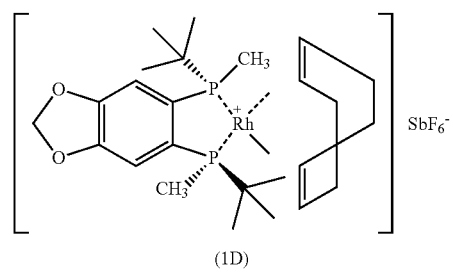

Under an argon atmosphere, to a dichloromethane solution (2 mL) of [Rh(cod)$_2$]SbF$_6$ (66 mg, 0.12 mmol) cooled to 0° C., a dichloromethane solution (3 mL) of (R,R)-1,2-bis(tert-butylmethylphosphino)-4,5-(methylenedioxy)benzene (Compound 1B) (50 mg, 0.15 mmol) was added dropwise. After stirring at room temperature for 30 minutes, most of the solvent was concentrated, and diethyl ether was added to precipitate crystals. The obtained crystals were filtered, washed with diethyl ether, and then dried to obtain ((R,R)-1,2-bis(tert-butylmethylphosphino)-4,5-(methylenedioxy)benzene) (1,5-cyclooctadiene)rhodium(1+)hexafluoroantimonate (Compound 1D) (66 mg, 0.09 mmol) as orange microcrystals in the yield of 71%.

Identification Data of Compound 1D $^1$H NMR (500 MHz, CDCl$_3$): δ 7.02 (m, 2H), 6.20 (s, 2H), 5.96 (t, J=7.2 Hz, 2H), 4.83 (m, 2H), 2.70-2.57 (m, 2H), 2.57-2.45 (m, 2H), 2.27-2.14 (m, 4H), 1.65 (d, J=8.6 Hz, 6H), 1.09 (d, J=14.9 Hz, 18H).

$^{31}$P NMR (202 MHz, CDCl$_3$): δ 55.8 (d, J=158 Hz).

Example 4

Asymmetric Hydrogenation Reaction

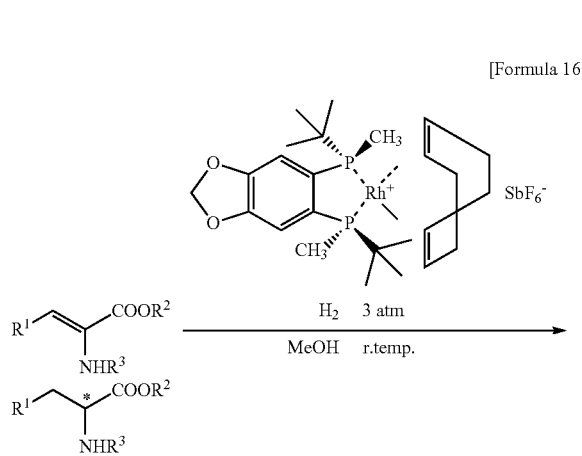

[Formula 16]

As a reaction substrate, 438.5 mg (2.00 mmol) of α-dehydroamino acid 2-(N-acetylamino)-3-phenyl-2-propenoicacid methyl ester, and as an asymmetric hydrogenation catalyst, 1.55 mg (2.00×10$^{-3}$ mmol) of ((R,R)-1,2-bis(tert-butylmethylphosphino)-4,5-(methylenedioxy)benzene)(1,5-cyclooctadiene)rhodium(1+)hexafluoroantimonate were added, hydrogen purge was performed five times, and 5 mL of dehydrated methanol degassed in advance was added. Subsequently, the hydrogen pressure was set to 3 atmospheres, and the reaction was then initiated. After 30 minutes of stirring at room temperature, the consumption of hydrogen in the vessel was stopped, and thus the reaction was assumed to be terminated. After the reaction liquid was concentrated, the remaining white crystals were dissolved in ethyl acetate and then, passed through a silica gel column. When the obtained eluate was analyzed with HPLC, (R)-2-(N-acetylamino)-3-phenylpropanoicacid methyl ester was obtained at an enantiomeric excess (ee) of 99.9%. Additionally, the compound was analyzed using $^1$H NMR, and the chemical yield was 99% or more (No. 1 in Table 1).

In this case, the HPLC conditions are as follows: HPLC: Daicel Chiralcel OJ, 1.0 mL/min, hexane:2-propanol=9:1

Retention time of each enantiomer (R)t$_1$=13.3 min, (S)t$_2$=19.3 min

Additionally, the asymmetric hydrogenation reaction was performed under the same conditions described above, except that types of reaction substrate and reaction conditions were changed as shown in Table 1, and the results are also shown in Table 1.

TABLE 1

| No. | R$^1$ | R$^2$ | R$^3$ | S/C | Reaction time | Chemical yield | Optical purity |
|---|---|---|---|---|---|---|---|
| 1 | Ph | Me | CH$_3$CO | 1,000 | 30 minutes | >99% | 99.9% ee |
| 2 | Ph | H | CH$_3$CO | 1,000 | 30 minutes | >99% | 99.5% ee |
| 3 | 3-FC$_6$H$_4$ | H | CH$_3$CO | 1,000 | 1 hour | >99% | 99.3% ee |
| 4 | H | Me | CH$_3$CO | 1,000 | 20 minutes | >99% | 99.9% ee |
| 5 | Furan-2-yl | Me | PhCH$_2$OCO | 200 | 3 hours | >99% | 97.9% ee |

S/C: Molar ratio between the substrate and the catalyst

Example 5

Asymmetric Hydrogenation Reaction

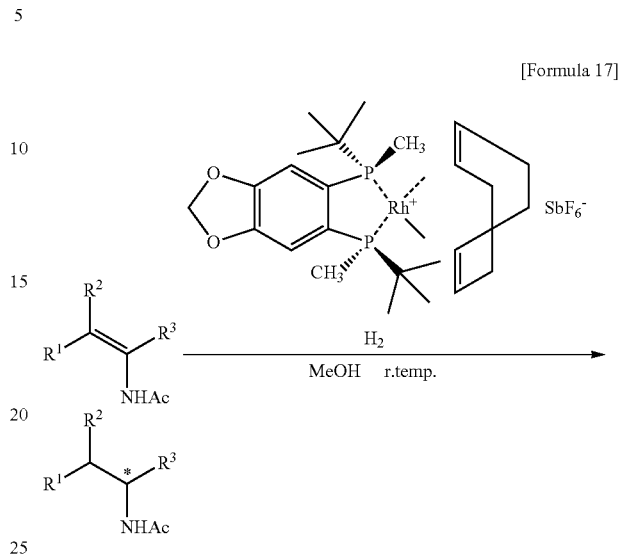

[Formula 17]

In a 50 mL glass autoclave, 314.3 mg (2.00 mmol) of β-dehydroamino acid(E)-methyl 3-acetamido-2-butenoate, and as an asymmetric hydrogenation catalyst, 1.55 mg (2.00×10$^{-3}$ mmol) of ((R,R)-1,2-bis(tert-butylmethylphosphino)-4,5-(methylenedioxy)benzene)(1,5-cyclooctadiene)rhodium(1+)hexafluoroantimonate were added, hydrogen purge was performed five times, and 5 mL of dehydrated methanol degassed in advance was added. Subsequently, the hydrogen pressure was set to 3 atmospheres, and the reaction was then initiated. After 40 minutes of stirring at room temperature, the consumption of hydrogen in the vessel was stopped, and thus the reaction was assumed to be terminated. After the reaction liquid was concentrated, the remaining white crystals were dissolved in ethyl acetate and then, passed through a silica gel column. When the obtained eluate was analyzed with GC, (R)-3-acetamidobutanoic acid methyl ester was obtained at an enantiomeric excess (ee) of 99.5%. Additionally, the compound was analyzed using $^1$H NMR, and the chemical yield was 99% or more (No. 1 in Table 2).

In this case, the GC analysis conditions are as follows:
GC: DEX CB, 135° C.

Retention time of each enantiomer (S)$_{t1}$=7.6 min, (R)$_{t2}$=8.1 min.

The asymmetric hydrogenation reaction was performed under the same condition described above, except that types of reaction substrate and reaction conditions were changed as shown in Table 2, and the results are also shown in Table 2.

TABLE 2

| No. | R$^1$ | R$^2$ | R$^3$ | S/C | Reaction time | Chemical yield | Optical purity |
|---|---|---|---|---|---|---|---|
| 1 | H | COOMe | Me | 1,000 | 40 minutes | >99% | 99.5% ee |
| 2 | COOMe | H | Me | 1,000 | 40 minutes | >99% | 98.5% ee |
| 3 | H | COOEt | n-Pr | 1,000 | 5 hours | >99% | 99.1% ee |
| 4 | COOEt | H | n-Pr | 1,000 | 3 hours | 88% | 96.8% ee |

TABLE 2-continued

| No. | $R^1$ | $R^2$ | $R^3$ | S/C | Reaction time | Chemical yield | Optical purity |
|---|---|---|---|---|---|---|---|
| 5 | COOEt | H | n-Pr | 1,000 | 24 hours | >99% | 93.1% ee |
| 6 | COOMe | H | Ph | 1,000 | 40 minutes | >99% | 95.4% ee |
| 7 | COOEt | H | p-MeOC$_6$H$_4$ | 1,000 | 3 hours | >99% | 97.7% ee |

S/C: Molar ratio between the substrate and the catalyst

INDUSTRIAL APPLICABILITY

According to the present invention, it is possible to provide a novel 1,2-bis(dialkylphosphino)-4,5-(methylenedioxy)benzene derivative that may form a useful metal complex as a catalyst for asymmetric synthesis reaction. Additionally, according to the production method of the present invention, this 1,2-bis(dialkylphosphino)-4,5-(methylenedioxy)benzene derivative can be easily produced. Furthermore, the metal complex having this 1,2-bis(dialkylphosphino)-4,5-(methylenedioxy)benzene derivative as a ligand has high enantioselectivity and reaction activity when used as a catalyst for an asymmetric synthesis reaction, and particularly, the metal complex having the novel 1,2-bis(dialkylphosphino)-4,5-(methylenedioxy)benzene derivative of the present invention has high asymmetric induction ability and catalytic activity on β-dehydroamino acid.

The invention claimed is:

1. A 1,2-bis(dialkylphosphino)-4,5-(methylenedioxy)benzene derivative represented by the following general formula (1):

[Formula 1]

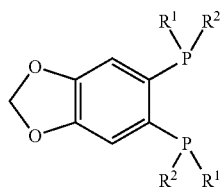

(1)

(wherein, $R^1$ and $R^2$ represent an alkyl group having 1 to 10 carbon atoms, and the number of carbon atoms of $R^1$ is different from that of $R^2$).

2. An optically active form of the 1,2-bis(dialkylphosphino)-4,5-(methylenedioxy)benzene derivative according to claim 1 represented by the following general formula (1A):

[Formula 2]

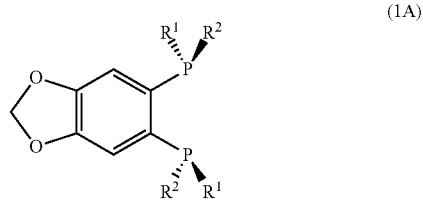

(1A)

(wherein, $R^1$ and $R^2$ represent an alkyl group having 1 to 10 carbon atoms, and the number of carbon atoms of $R^1$ is different from that of $R^2$).

3. The 1,2-bis(dialkylphosphino)-4,5-(methylenedioxy)benzene derivative according to claim 1, wherein $R^1$ is a t-butyl group and $R^2$ is a methyl group, or $R^1$ is a methyl group and $R^2$ is a t-butyl group.

4. A method for producing the 1,2-bis(dialkylphosphino)-4,5-(methylenedioxy)benzene derivative according to claim 1, comprising steps of: deboranating a phosphine-borane compound represented by the following general formula (2), subsequently reacting the deboranated compound with an alkyl magnesium halide compound, then, reacting the product with an alkyldihalogenophosphine represented by the general formula: $R^aPX'_2$ ($R^a$ is one of $R^1$ and $R^2$ in the general formula (1), and X' represents a halogen atom), and subsequently, reacting the product with a Grignard reagent represented by the general formula: $R^bMgX''$ ($R^b$ is one of $R^1$ and $R^2$ in the general formula (1), and X'' represents a halogen atom):

[Formula 3]

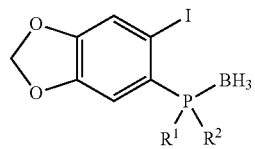

(2)

(wherein, $R^1$ and $R^2$ represent an alkyl group having 1 to 10 carbon atoms, and the number of carbon atoms of $R^1$ is different from that of $R^2$).

5. A method for producing the optically active 1,2-bis(dialkylphosphino)-4,5-(methylenedioxy)benzene derivative according to claim 2, comprising steps of: deboranating an optically active phosphine-borane compound represented by the following general formula (2A), subsequently reacting the deboranated compound with an alkyl magnesium halide compound, then, reacting the product with an alkyldihalogenophosphine represented by the general formula: $R^aPX'_2$ ($R^a$ is one of $R^1$ and $R^2$ in the general formula (1A), and X' represents a halogen atom), and subsequently, reacting the product with a Grignard reagent represented by the general formula: $R^bMgX''$ ($R^b$ is one of $R^1$ and $R^2$ in the general formula (1A), and X'' represents a halogen atom):

[Formula 4]

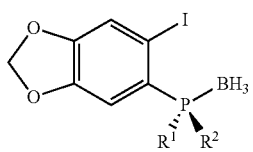

(2A)

(wherein, $R^1$ and $R^2$ represent an alkyl group having 1 to 10 carbon atoms, and the number of carbon atoms of $R^1$ is different from that of $R^2$).

6. A 1,2-bis(dialkylphosphino)-4,5-(methylenedioxy)benzene-borane derivative represented by the following general formula (1-1):

[Formula 5]

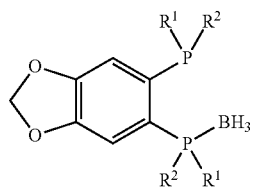

(1-1)

(wherein, $R^1$ and $R^2$ represent an alkyl group having 1 to 10 carbon atoms, and the number of carbon atoms of $R^1$ is different from that of $R^2$).

7. An optically active 1,2-bis(dialkylphosphino)-4,5-(methylenedioxy)benzene-borane derivative represented by the following general formula (1-1A):

[Formula 6]

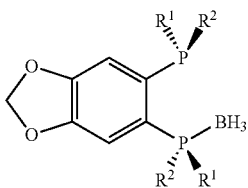

(1-1A)

(wherein, $R^1$ and $R^2$ represent an alkyl group having 1 to 10 carbon atoms, and the number of carbon atoms of $R^1$ is different from that of $R^2$).

8. A method for producing a 1,2-bis(dialkylphosphino)-4,5-(methylenedioxy)benzene-borane derivative represented by the following general formula (1-1), wherein a 1,2-bis(dialkylphosphino)-4,5-(methylenedioxy)benzene derivative represented by the general formula (1) and a boranating agent selected from borane-THF complexes, alkali metal borohydrides, and borane-amine complexes are reacted:

[Formula 7]

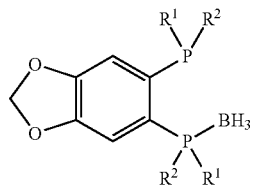

(1-1)

(wherein, $R^1$ and $R^2$ represent an alkyl group having 1 to 10 carbon atoms, and the number of carbon atoms of $R^1$ is different from that of $R^2$).

9. A method for producing an optically active 1,2-bis(dialkylphosphino)-4,5-(methylenedioxy)benzene-borane derivative represented by the following general formula (1-1A), wherein an optically active 1,2-bis(dialkylphosphino)-4,5-(methylenedioxy)benzene derivative represented by the general formula (1A) and a boranating agent selected from alkali metal borohydrides and borane-amine complexes are reacted:

[Formula 8]

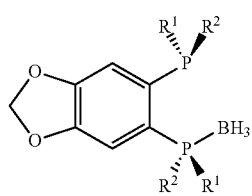

(1-1A)

(wherein, $R^1$ and $R^2$ represent an alkyl group having 1 to 10 carbon atoms, and the number of carbon atoms of $R^1$ is different from that of $R^2$).

10. A metal complex having the 1,2-bis(dialkylphosphino)-4,5-(methylenedioxy)benzene derivative according to claim 1 as a ligand.

11. The metal complex according to claim 10, wherein the 1,2-bis(dialkylphosphino)-4,5-(methylenedioxy)benzene derivative is the optically active 1,2-bis(dialkylphosphino)-4,5-(methylenedioxy)benzene derivative and is used as an asymmetric synthesis catalyst.

12. An asymmetric hydrogenation method, wherein the metal complex of the 1,2-bis(dialkylphosphino)-4,5-(methylenedioxy)benzene derivative according to claim 11 is used as a catalyst.

13. The 1,2-bis(dialkylphosphino)-4,5-(methylenedioxy)benzene derivative according to claim 2, wherein $R^1$ is a t-butyl group and $R^2$ is a methyl group, or $R^1$ is a methyl group and $R^2$ is a t-butyl group.

* * * * *